United States Patent [19]

Rechner et al.

[11] Patent Number: 5,550,278
[45] Date of Patent: Aug. 27, 1996

[54] PROCESS FOR WORKING UP THE LIQUID REACTION PRODUCTS FROM THE CU-CATALYSED PREPARATION OF DIMETHYL CARBONATE

[75] Inventors: Johann Rechner, Krefeld; Paul Wagner, Düsseldorf; Hans-Josef Buysch, Krefeld; Alexander Klausner, Köln, all of Germany

[73] Assignee: Bayer Aktiengesellschaft, Leverkusen, Germany

[21] Appl. No.: 340,775

[22] Filed: Nov. 17, 1994

[30] Foreign Application Priority Data

Nov. 24, 1993 [DE] Germany .......................... 43 39 977.0

[51] Int. Cl.⁶ ..................................................... C07C 69/96
[52] U.S. Cl. ................................................ 558/277; 558/26
[58] Field of Search ............................................... 558/277

[56] References Cited

U.S. PATENT DOCUMENTS

| | | | |
|---|---|---|---|
| 3,803,201 | 4/1974 | Gilpin et al. | 558/277 |
| 3,846,468 | 11/1974 | Perrotti et al. | 558/270 |
| 3,963,586 | 6/1976 | Ginnasi et al. | 558/277 |
| 4,162,200 | 7/1979 | Himmele et al. | 558/277 |
| 4,218,391 | 8/1980 | Romano et al. | 558/277 |
| 4,318,862 | 3/1982 | Romano et al. | 558/277 |
| 4,370,275 | 1/1983 | Stammann et al. | 558/277 |
| 5,142,087 | 8/1992 | Joerg et al. | 558/277 |
| 5,274,163 | 12/1993 | Rechner et al. | 558/277 |

FOREIGN PATENT DOCUMENTS

| | | |
|---|---|---|
| 0217651 | 4/1987 | European Pat. Off. . |
| 0460732 | 12/1991 | European Pat. Off. . |
| 0460735 | 12/1991 | European Pat. Off. . |
| 2110194 | 11/1971 | Germany . |
| 2450856 | 4/1975 | Germany . |
| 2607003 | 9/1976 | Germany . |
| 2743690 | 4/1978 | Germany . |
| 3045767 | 6/1981 | Germany . |
| 3926709 | 2/1991 | Germany . |
| 4203796 | 8/1993 | Germany . |
| 1470160 | 4/1977 | United Kingdom . |

*Primary Examiner*—Gary Geist
*Assistant Examiner*—Dwayne C. Jones
*Attorney, Agent, or Firm*—Sprung Horn Kramer & Woods

[57] ABSTRACT

A process is described for working up liquid reaction mixtures such as are formed during dimethyl carbonate preparation by oxidative carbonylation of methanol in the presence of a copper-containing catalyst, which process permits a simple separation of the water of reaction from the dimethyl carbonate. In this process, in a first distillation column, the water of reaction is taken from the bottom of the column; the top product from the first column is separated in a second column, under increased pressure, into dimethyl carbonate as bottom product and into a top product which is predominantly composed of methanol. The top product from the distillative working-up in the second column, which is predominantly composed of methanol, is recycled to the reaction process.

16 Claims, 2 Drawing Sheets

PROCESS FOR WORKING UP THE LIQUID REACTION PRODUCTS FROM THE CU-CATALYSED PREPARATION OF DIMETHYL CARBONATE

BACKGROUND OF THE INVENTION

1. Field of the Invention

The present invention relates to a process for working up liquid reaction mixtures such as are formed during dimethyl carbonate preparation by oxidative carbonylation of methanol in the presence of a copper-containing catalyst under increased pressure at elevated temperature, which is characterized in that the reaction solution obtained after removal of the catalyst is freed from the water of reaction by simple distillation under normal pressure, and the anhydrous top product, comprising methanol and dimethyl carbonate, is separated by distillation under increased pressure into pure dimethyl carbonate as the bottom product and a dimethyl carbonate-depleted mixture of methanol and dimethyl carbonate as the top product, from which the top product is recycled to the normal-pressure column or the reaction.

2. Description of the Related Art

In the past, a number of processes have been developed for the preparation of dialkyl carbonates by catalytic reaction of the starting materials methanol, carbon monoxide and oxygen.

In DE-A 2 110 194, metal complexes of groups IB, IIB and VIIIB of the Periodic Table, in particular the metals Cu, Ag, Au, Zn, Cd, Hg, Fe, Co and Ni, which can exist in two different oxidation levels in redox reactions, have been mentioned as suitable catalysts. This process gives good yields with complexed $Cu_2Cl_2$, but has the disadvantage that the removal of the very expensive complex ligands and of the dissolved complexed catalyst from the reaction solution requires much effort.

In DE-PC 2 743 690, simple monovalent salts of copper are used as catalysts instead of the copper complex compounds. Although this process variant gives good yields of dialkyl carbonates, working-up of the reaction solution also presents major problems here, since the partly dissolved catalyst must be removed from the reaction solution. According to the doctrine of this patent, this is effected by filtering off of the suspended content and rectification or crystallization of the dissolved catalyst. Since the catalyst-containing reaction solutions carry the catalyst to other parts of the plant, a high expenditure on apparatus is necessary for working up the reaction solution and catalyst. Because of the corrosive properties, all apparatuses (tanks, pipelines, distillation, crystallization and filtration apparatuses) which come into contact with the catalyst must be made of corrosion-resistant material. The process thereby loses its attractiveness.

The same working-up problems mean that the use of synthesis gas instead of CO, as described in DE-C 3 045 767, must remain economically unattractive. The corrosion problems during working-up of the reaction solution caused by the copper-containing catalyst render processes which comprise further additions to the catalyst (for example EP-A 217 651, EP-B 090 977, U.S. Pat. No. 4,370,275) uneconomical.

An alternative in process technology for removal of the catalyst is disclosed in DE-A 3 926 709. In this process the copper-containing catalyst remains in the reactor. The dialkyl carbonate formed during the reaction is stripped from the reaction mixture by the reaction gas together with the water of reaction and methanol. This effect is in general achieved by passing through the reaction mixture a gas stream of 20 to 30 standard 1 of $CO/O_2$ gas mixture per g of copper present as copper catalyst in the reactor. Disadvantages of this process are the very large amounts of gas which must be kept circulating, and the high energy costs thereby caused, as well as the problems in dispersion of the gas because of the large amounts of gas. In this procedure, the temperature and pressure of the reactor must additionally be regulated precisely in order to be able to maintain the level of liquid in the reactor, since even small variations in reactor temperature or pressure lead to the amounts discharged being changed significantly. The statements made in the case of DE-A 3 926 709 essentially apply to the processes described in EP 0 460 732 A1 and EP 0 460 735 A2.

In all these processes, although the catalyst is removed more or less effectively, the process problems during working-up of the catalyst-free reaction solution also have not been solved in these Applications, that is to say removal of the water from the catalyst-free reaction solution and the separation of methanol and dimethyl carbonate (DMC), since these form an azeotrope.

According to DE-A 2450856, the removal of dimethyl carbonate from the water of reaction and methanol (MeOH) by means of a simple rectification is complicated, since various azeotropes form between DMC, MeOH and water. The doctrine of the patent application is separation by using extractive distillation with water as the solvent. However, the process is uneconomical, since considerable amounts of water are required for the separation (9.5 g of water per g of reaction solution).

DE-A 2607003 describes a separation experiment for splitting the methanol/dimethyl carbonate azeotrope by applying pressure and elevated temperature. According to the doctrine of this application, although a bottom fraction of pure DMC is obtained, the top product is again a mixture of methanol and DMC which is depleted in DMC. How such a process fragment can be integrated appropriately into a working-up process is not disclosed. In addition, the separation is carried out without the water unavoidably obtained during oxidative carbonylation, which, as disclosed in DE-A 3926709, forms a ternary azeotrope with methanol and dimethyl carbonate.

U.S. Pat. No. 4,162,200 also discloses a distillation by extraction where, for example, cyclohexane and chlorobenzene are employed as auxiliaries. Because of the use of reagents foreign to the system, additional distillation steps become necessary and these again impede an economic solution to the separation problem. In addition, these substances foreign to the system can lead to contamination of the dimethyl carbonate. A corrosive action is to be expected in particular if chlorobenzene is used, which leads to considerably higher costs.

U.S. Pat. No. 3,803,201 describes a process in which the methanol/DMC azeotrope is worked up by a combination of low temperature crystallization, filtration and subsequent fractional distillation. This process is unusable for an industrial application merely because of the temperature of about −70° C. required. The use of crystallization, filtration and distillations furthermore represents a considerable expenditure on apparatus, which makes the process look uneconomical.

The object was to discover a simple and inexpensive process for the working-up of reaction solutions of dimethyl carbonate, methanol and water such as are formed during oxidative carbonylation of methanol using copper chloride as the catalyst.

SUMMARY OF THE INVENTION

Surprisingly, it has now been found that the water of reaction and dimethyl carbonate can be isolated from the reaction solutions, such as are formed during oxidative carbonylation of methanol using copper chloride as the catalyst, by the combination of normal-pressure distillation with distillation under increased pressure, instead of by cumbersome crystallization, filtration and distillation or by extractive distillation. This combination of normal-pressure distillation for removal of the water and subsequent pressure distillation of the anhydrous reaction solution for isolation of the dimethyl carbonate and recycling of the methanolic top product to the reactions is not only a simple process but, surprisingly, is also very inexpensive. This solution to the problem was all the more surprising since the effect of pressure distillation on the problematic component, DMC-methanol, was indeed known but was not classified as useful, and according to the prior art the assistance of an extraction agent or crystallization with subsequent filtration and distillation is necessary, since the DMC/methanol/water mixture obtained in the reaction could not be worked up by the pressure distillation described for the DMC/methanol mixture.

The present invention relates to a process for the preparation of dimethyl carbonate by reaction of methanol with oxygen and carbon monoxide in the presence of a copper-containing catalyst suspended or dissolved in the reaction medium under increased pressure at elevated temperature, removal of the catalyst and working-up of the reaction solution, which is characterized in that the catalyst-free solution is initially freed from the water of reaction as the bottom product in a first distillation column and the top product, comprising dimethyl carbonate and methanol, is separated in a subsequent pressure distillation at elevated temperature under increased pressure into a bottom product of pure dimethyl carbonate and a dimethyl carbonate-depleted, methanolic top product, and the top product is recycled to the process.

BRIEF DESCRIPTION OF THE DRAWINGS

The accompanying FIG. 2 is especially referred to in the working example.

DETAILED DESCRIPTION OF THE INVENTION

Figure 1:
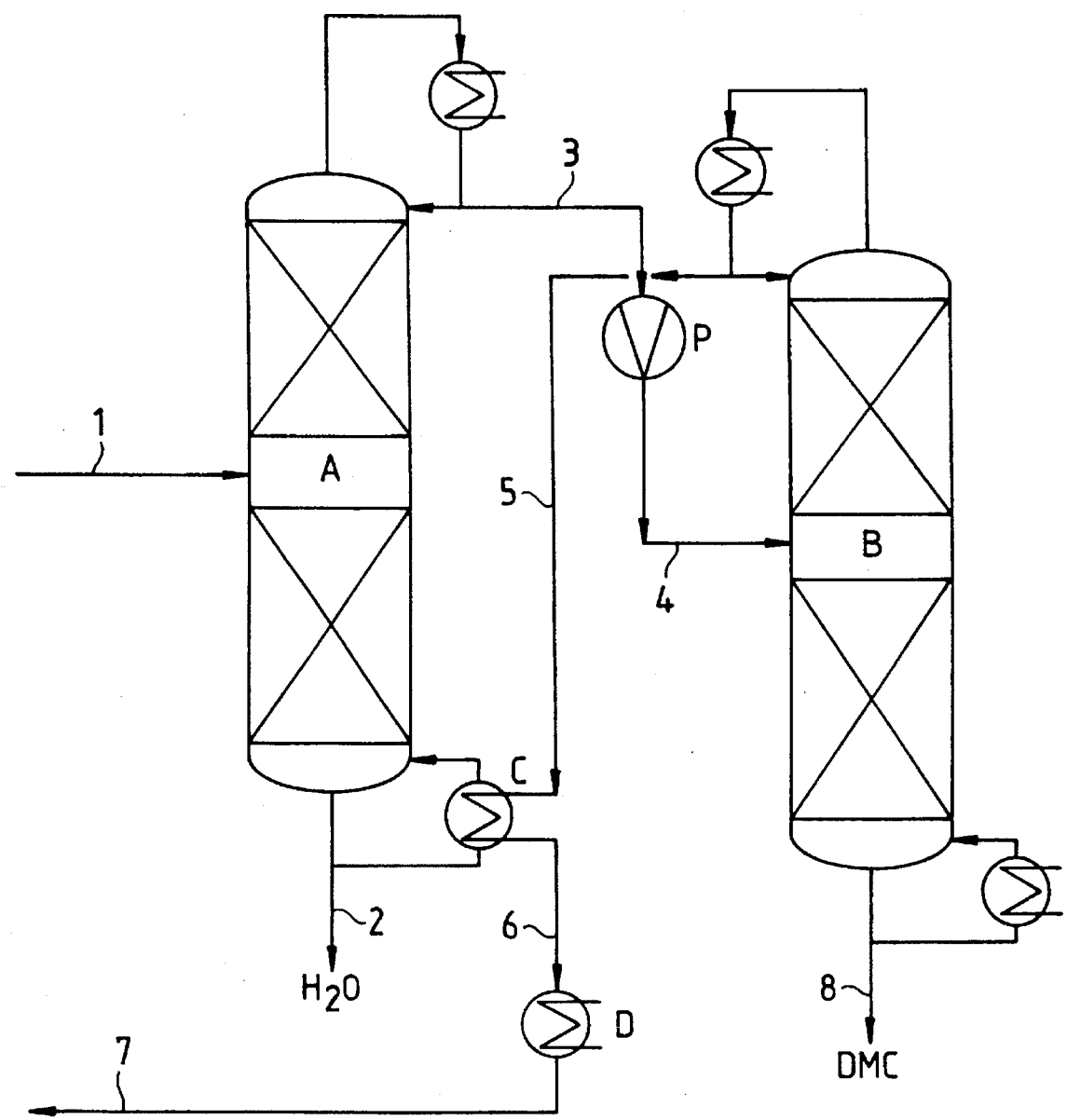
FIGS. 1 and 2 show a variant of how to carry out the inventive process.

In the process according to the invention, which is preferably carried out continuously, the methanol to be reacted is brought into contact with the reaction gases oxygen and carbon monoxide, and if necessary additionally an inert gas, in the reactor in the presence of the catalyst.

Copper compounds based on copper(I) and/or copper(II) salts are used as catalysts in the process according to the invention. Since the reaction is a redox reaction, both copper ion species are present during the reaction. Copper catalysts which are preferably employed are copper(I) halides, copper(I) acetylacetonate, copper(I) sulphate and/or copper(II) alkoxyhalides, copper(II) alkoxysulphate and copper(II) alkoxyacetylacetonate, and copper(II) methoxychloride is particular preferably employed.

The liquid reaction medium essentially comprises the methanol to be reacted. In general, the molar ratio of methanol:dimethyl carbonate:copper (copper from the catalyst suspended and/or dissolved in the reaction mixture), standardized to 1 with respect to the methanol content, during continuous operation in the reactor is 1:(0.005–1):(0.001–5), advantageously 1:(0.02–0.5):(0.005–1) and particularly preferably 1:(0.04–0.3):(0.01–0.16).

The reaction of the reaction gases with the methanol is carried out at a temperature from 60° to 200° C., preferably from 80° to 140° C., particularly preferably from 100° to 130° C. The reaction is carried out under pressures of 1 to 60 bar, preferably under 10 to 40 bar and particularly preferably under 15 to 35 bar. The pressure is expediently produced by forcing in the reaction gases.

The gas stream fed to the reactor can be varied within wide limits, but a total gas stream comprising CO, oxygen and, if appropriate, an inert gas (such as, for example: $N_2$, $CO_2$ and the like), based on the copper of the catalyst present in the reaction solution, of 0.2–100 standard l/hour and g of Cu, preferably 0.6 to 80 standard l/hour and g of Cu, particularly preferably 0.8 to 5 standard l/hour and g of Cu, is expediently established.

The composition of the reaction gases carbon monoxide and oxygen can be varied within wide concentration limits, but a $CO:O_2$ molar ratio (standardized to CO) of 1:(0.005–1.0), and preferably of 1:(0.02–0.5), is expediently established. The oxygen partial pressure at these molar ratios is high enough to be able to achieve high space/time yields, and at the same time to allow no explosive carbon monoxide/oxygen gas mixtures to be formed. The reaction gases are not subject to particular purity requirements, and synthesis gas can thus serve as the CO source and air as the $O_2$ carrier, but it should be ensured that no catalyst poisons, such as, for example, sulphur or compounds thereof, are introduced.

The reaction of the catalyst-containing methanol with the reaction gases under the reaction conditions is expediently carried out at the lowest possible concentration of the water of reaction unavoidably obtained in the reaction mixture, in order to avoid secondary reactions, such as the formation of carbon dioxide and the simultaneous deactivation of the copper catalyst. The concentration of the water of reaction is in general not more than 8% by weight, advantageously not more than 6% by weight, based on the liquid phase.

The conversion is carried out up to a desired and adjustable value, based on the methanol employed, of less than 35% and particularly preferably less than 25%.

The catalyst can be removed in various ways in the process according to the invention.

In a preferred embodiment, the catalyst is removed continuously from the reactor together with the reaction solution and separated off by sedimentation, as described in DE-A 4203796, and the catalyst-free reaction solution is fed to the working-up.

In another preferred embodiment of the process according to the invention, the reaction solution is stripped continuously from the reactor with the aid of the excess reaction gas, as described in EP 0460732 A1, EP 0460735 A2 and DE-A 3926709 A1 and is thus obtained in catalyst-free form after subsequent condensation.

The reaction solutions which can be worked up according to the invention comprise methanol to the extent of 50 to 90% by weight, preferably to the extent of 55 to 80% by weight and particularly preferably to the extent of 60 to 75% by weight; and dimethyl carbonate to the extent of 8 to 45% by weight, preferably 15 to 40% by weight and particularly preferably to the extent of 20 to 37% by weight. The water content of these reaction solutions is between 0.5 and 15% by weight, preferably between 1 and 10% by weight, particularly preferably between 1.5 and 8% by weight. All the data are based on the total weight of the reaction solution.

According to the invention, the catalyst-free reaction solutions thus obtained are initially freed from the water of reaction by simple rectification. The rectification is initially carried out under 0.1 to 8 bar, preferably 0.5 to 4 bar and particularly preferably under 0.8 to 3 bar. The bottom of the column here is heated up to 65° to 200° C., preferably 80° to 160° C. and particularly preferably to 90°–150° C.

DMC and methanol are obtained as the top product and water is obtained as the bottom product. In contrast to the known literature, no DMC/MeOH/$H_2O$ or DMC/$H_2O$ azeotrope was obtained, but separation of the DMC and methanol from the water of reaction was achieved.

On the basis of the reaction solution composition sought in the reaction, DMC/MeOH is initially distilled off selectively as an azeotrope in the distillation, followed by MeOH, which forms no azeotrope with water.

In the preferred embodiment of the separation, a mixture of DMC and MeOH is obtained as the top product and water is obtained as the bottom product. The top product comprising DMC and MeOH still has a water content of less than 1% by weight, and preferably less than 0.1% by weight of water.

To separate the DMC and MeOH, the DMC/MeOH mixture is then separated by distillation in a pressure column, without addition of an auxiliary, into pure DMC as the bottom product and a DMC-depleted methanolic top product. The DMC thus obtained already has such a high purity that it can be employed for most applications without further purification.

The rectification is carried out under 1 to 30 bar, preferably 4 to 20 bar and particularly preferably under 8 to 15 bar. The bottom of the column here is heated up to 65° to 250° C., preferably 100° to 220° C. and particularly preferably to 130° to 200° C.

The top product of the pressure column is recycled to the process. For this, in the preferred embodiment of the process according to the invention, this top product can be recycled to the reactor, if appropriate together with fresh methanol.

In another embodiment, this top product of the pressure column is recycled to a suitable point in the first column operating under normal pressure.

In yet another embodiment, the top product of the pressure distillation can be fed to the reactor of another working-up column before the recycling. In this other working-up column, the azeotrope of dimethyl carbonate and methanol is obtained as the top product and is recycled to a corresponding point in the pressure column. Methanol comprising more than 90% by weight, preferably more than 95% by weight, particularly preferably more than 98% by weight of methanol is obtained as the bottom product and is recycled to the reactor.

Columns having fixed baffles, fillings and packings are suitable distillation columns for these separation processes. The fillings or ordered packings to be used are those which are customary per se for distillations, such as are described, for example, in Ullmanns Encyclopädie der Techn. Chemie (Ullmann's Encyclopaedia of Industrial Chemistry), 4th Edition, Volume 2, page 528 et seq. Examples which may be mentioned are: Raschig or Pall rings, Berl, Intalex or torus saddles or interpacking. These fillings can be made of various materials, such as glass, stoneware, porcelain, stainless steel, plastic and metal, which can be processed in woven or mesh form, especially if metal is used. Preferred fillings or packings are, for example, Pall and Novolax rings, Berl saddles, BX packing, Montz-Pak, Metal-pak, Melladur, Kerepak and CY packing.

Suitable tray columns are, for example, perforated trays, bubble trays, valve trays, tunnel trays and centrifugal trays, which in turn can be of various designs.

Columns having fillings or packings are particularly suitable for the column for removal of the water. The number of theoretical plates is 1 to 200, preferably 5 to 100, particularly preferably 10 to 60.

Both tray and filled or packed columns are suitable for the pressure distillation column. The number of theoretical plates is 1 to 200, preferably 5 to 100, particularly preferably 10 to 60.

FIG. 1 shows the process according to the invention by way of example:

The catalyst-free reaction solution comprising methanol, dimethyl carbonate and water is introduced via line 1 into the middle third of column A. The water of reaction which has been removed leaves the column as the bottom product via line 2. The top product, comprising dimethyl carbonate and methanol, is metered via line 3, pump P and line 4 into the middle third of pressure column B. The methanolic top product depleted in dimethyl carbonate leaves the pressure column via line 5 and heats the bottom of column A via heat exchanger C. After leaving heat exchanger C, the top product is further cooled, if appropriate, in heat exchanger D and recycled to the reaction via line 7. The useful product dimethyl carbonate leaves column B via line 8 and is of adequate purity for most cases of use.

The invention is illustrated in more detail by the following example, but without being limited thereto.

EXAMPLE 1

Figure 2:
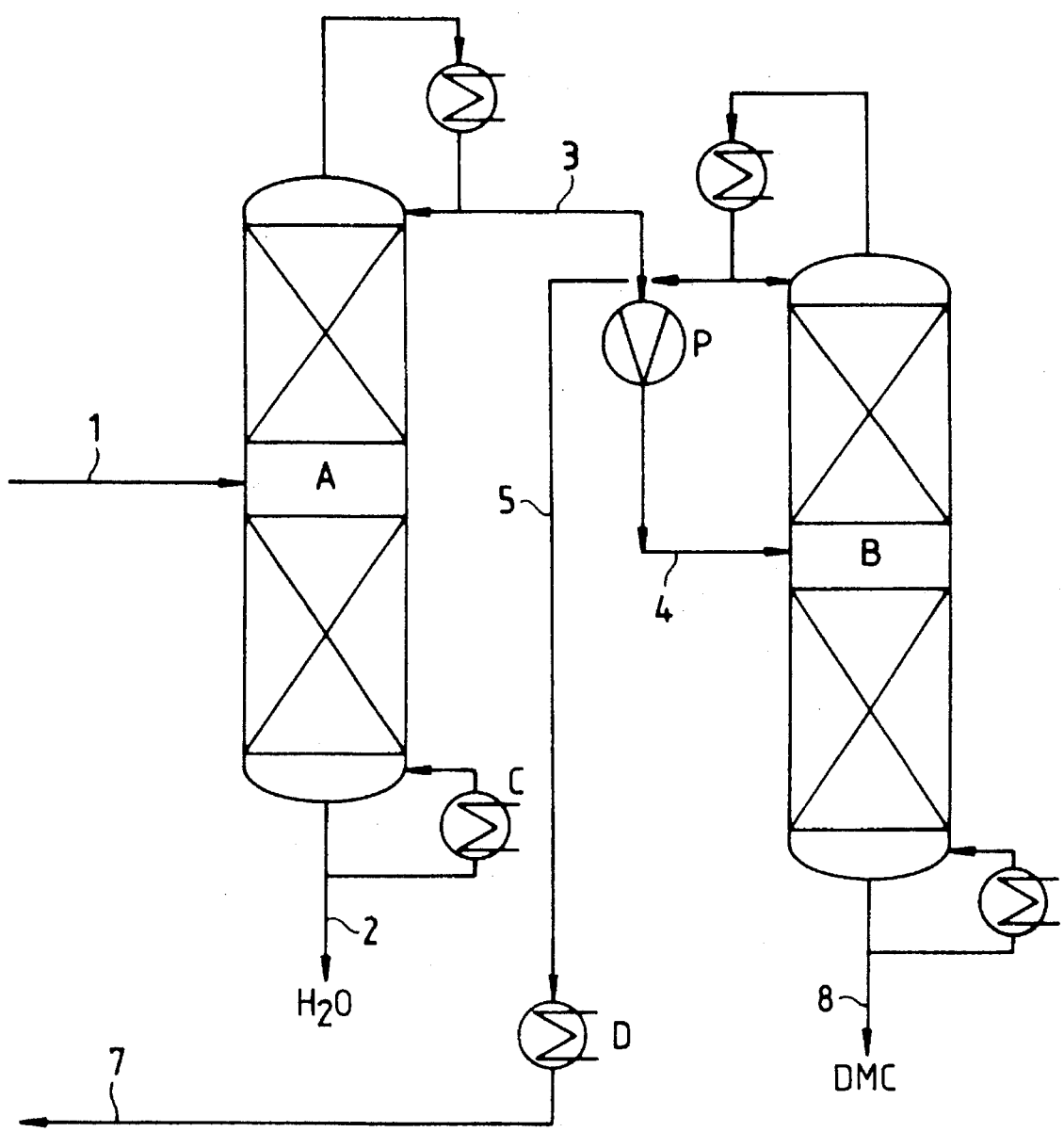

An apparatus as shown in FIG. 2 is used. FIG. 2 differs from FIG. 1 in that line 5 is not connected to heat exchanger C. The catalyst-free reaction solution was metered into the middle of the first distillation column A. This distillation column of glass (d=4.5 cm, 1=60 cm) for removal of the water was filled with 800 ml of 4×4 mm $V_4A$ wire mesh coils and had an oil-heated bottom evaporator with a discharge and an attached condenser with reflux divider. The top product from A was metered via a buffer vessel and a pump into the middle of pressure column B. Pressure column B was identical to the glass column A in structure, but with the difference that it was made of steel and had a pressure retention system which allowed precise regulation of the pressure.

The apparatus was charged with 560 g/hour of a reaction mixture comprising 66% by weight of methanol, 31% by weight of dimethyl carbonate and 3% by weight of water. Column A operated under normal pressure and had a bottom temperature of 100° C. Column B was operated under a pressure of 10 bar and had a bottom temperature of 185° C. After 6 hours, the apparatus was in equilibrium and gave 16.6 g per hour of water of reaction as the bottom discharge of A. Distillation column B produced 75.5 g/hour of DMC having a purity of 99.89%, and the top product of B was 469.4 g/hour and comprised methanol to the extent of 79.1% by weight and DMC to the extent of 20.9% by weight. The water content of this return stream was about 250 ppm.

What is claimed is:

1. A process for the preparation of dimethyl carbonate by reaction of methanol with oxygen and carbon monoxide in the presence of a copper-containing catalyst suspended or dissolved in the reaction medium under increased pressure at elevated temperature, removal of the catalyst and working-up of the reaction solution, wherein the catalyst-free reaction solution is initially freed from the water of reaction as the bottom product in a first distillation column and the top product, comprising dimethyl carbonate and methanol, is separated in a subsequent pressure distillation at elevated temperature under increased pressure into a bottom product of pure dimethyl carbonate and a dimethyl carbonate-depleted, methanolic top product, and the top product is recycled to the reaction medium and not to the distillation column.

2. The process of claim 1, wherein the catalyst-free reaction solution comprises, based on its total weight, methanol to the extent of 50–90% by weight, dimethyl carbonate to the extent of 8–45% by weight, and water to the extent of 0.5–15% by weight.

3. The process of claim 2, wherein the catalyst-free reaction solution comprises, based on its total weight, methanol to the extent of 55–80% by weight, dimethyl carbonate to the extent of 15–40% by weight, and water to the extent of 1–10% by weight.

4. The process of claim 3, wherein the catalyst-free reaction solution comprises, based on its total weight, methanol to the extent of 60–75% by weight, dimethyl carbonate to the extent of 20–37% by weight, and water to the extent of 1.5–8% by weight.

5. The process of claim 1, wherein the first distillation column for removal of the water is operated under 0.1 to 8 bar, and for this the bottom of the column is heated up to 65° to 200° C.

6. The process of claim 5, wherein the first distillation column for removal of the water is operated under 0.5 to 4 bar, and for this the bottom of the column is heated up to 80° to 160° C.

7. The process of claim 6, wherein the first distillation column for removal of the water is operated under 0.8 to 3 bar, and for this the bottom is heated up to 90° to 150° C.

8. The process of claim 1, wherein the top product of the first distillation column is introduced into a second distillation column and separated under 1 to 30 bar at a column bottom temperature of 65° to 250° C., and pure DMC is removed as the bottom product.

9. The process of claim 8, wherein the pressure is 4 to 20 bar and the bottom temperature is 100°–220° C.

10. The process of claim 9, wherein the pressure is 8 to 15 bar and the bottom temperature is 130° to 200° C.

11. The process of claim 1, wherein columns with fillings or packings are employed as distillation columns for removal of the water, the number of theoretical plates being 1 to 200.

12. The process of claim 11, wherein the number of theoretical plates is 5 to 100.

13. The process of claim 12, wherein the number of theoretical plates is 10 to 60.

14. The process of claim 1, wherein tray, filled or packed columns are employed as distillation columns for the pressure distillation, the number of theoretical plates being between 1 and 200.

15. The process of claim 14, wherein the number of theoretical plates is 5 to 100.

16. The process of claim 15, wherein the number of theoretical plates is 10 to 60.

* * * * *